(12) United States Patent
Wilbur et al.

(10) Patent No.: US 6,492,560 B2
(45) Date of Patent: Dec. 10, 2002

(54) DISCRETE-LENGTH POLYETHYLENE GLYCOLS

(75) Inventors: D. Scott Wilbur, Edmonds; Pradip M. Pathare, Seattle, both of WA (US)

(73) Assignee: The University of Washington, Seattle, WA (US)

( * ) Notice: Subject to any disclaimer, the term of this patent is extended or adjusted under 35 U.S.C. 154(b) by 0 days.

(21) Appl. No.: 09/962,840

(22) Filed: Sep. 24, 2001

(65) Prior Publication Data

US 2002/0091288 A1 Jul. 11, 2002

Related U.S. Application Data

(63) Continuation of application No. 09/062,286, filed on Apr. 17, 1998, now Pat. No. 6,294,697, which is a continuation of application No. PCT/US96/16760, filed on Oct. 18, 1996.
(60) Provisional application No. 60/005,599, filed on Oct. 19, 1995.

(51) Int. Cl.$^7$ ............................................. C07C 211/03
(52) U.S. Cl. ....................... 564/505; 564/502; 564/503; 564/504; 564/511; 564/512; 514/668; 514/674; 514/663; 514/666
(58) Field of Search ................................. 564/505, 502, 564/503, 504, 511, 512; 514/663, 666, 668, 674; 528/335

(56) References Cited

U.S. PATENT DOCUMENTS 5,128,441 A    7/1992  Speranza et al.

FOREIGN PATENT DOCUMENTS

| EP | 0 301 706 | 1/1989 |
| EP | 0 335 972 A1 | 11/1989 |
| WO | WO 95/25763 | 9/1995 |

OTHER PUBLICATIONS

Bonina, F.P., et al., "In vitro and in vivo evaluation of polyoxyethylene indomethacin esters as dermal prodrugs," *Journal of Controlled Release*, vol. 34, No. 3, Jun. 1995, pp. 223–232.

Burnham, N., "Polymers for delivering peptides and proteins," *American Journal of Hospital Pharmacy*, vol. 51, No. 2, Jan. 15, 1994 pp. 210–218.

Cunningham–Rundles, C., et al., "Biological activities of polyethylene–glycol immunoglobulin conjugates," *Journal of Immunological Methods*, vol. 152, No. 2, Aug. 10, 1992, pp. 177–190.

Degado, Cristina et al., "The Uses and Properties of PEG–Linked Proteins," *Crit. Rev. Ther. Drug Carrier Systems*, vol. 9, 1992, pp. 249–304.

Felix, A.M., et al. "Enhanced biological activity of site–directed pegylated GRF analogs," *International Journal of Peptide Protein Research*, vol. 46, No. 1, Jul. 1995, pp. 253–264.

Hershfield, M.S., "PEG–ADA Replacement Therapy for Adenosine Deaminase Deficiency: An Update after 8.5 Years," *Clinical Immunology and Immunopathology*, vol. 76, No. 3, Sep. 1995, pp. S228–S232.

Jaschke, A., et al., "Synthesis and properties of oligodeoxyribonucleotide–polyethylene gycol conjugates," *Nucleic Acids Research*, vol. 22, 1994, pp. 4810–4817.

Jensen, P.–K.E., et al., "Enteral Bioavailability of Human Granulocyte Colony Stimulating Factor Conjugated with Poly(ethylene glycol)," *Pharm. Res.*, vol. 13, 1996, pp. 102–107.

Kusstatscher, S., et al., "Different Molecular Forms of Basic Fibroblast Growth Factor (bFGF) Accelerate Duodenal Ulcer Healing in Rats," *Journal of Pharmacology and Experimental Therapeutics*, vol. 275, No. 1, Oct. 1995, pp. 456–461.

Mast, A.E., et al., "Evaluation of the rapid plasma elimination of recombinant $\alpha_1$–proteinase inhibitor: Synthesis of polyethylene glycol conjugates with improved therapeutic potential," *Journal of Laboratory and Clinical Medicine*, vol. 116, No. 1, Jul. 1990, pp. 58–65.

Menzel, T., et al., "Clinical and Preclinical Evaluation of Recombinant PEG–IL–2 in Human," *Cancer Biotherapy*, vol. 8, No. 3, 1993, pp. 199–212.

Roseng, L., et al., "Uptake, Intracellular Transport, and Degradation of Polyethylene Glycol–modified Asialofetuin in Hepatocytes," *Journal of Biological Chemistry*, vol. 267, No. 32, 1992, pp. 22987–22993.

Saiki, I., et al., "Antimetastatic Activity of Polymeric RGDT Peptides Conjugated with Poly(ethylene glycol)," *Japanese Journal of Cancer Research*, vol. 84, No. 5, May 1993, pp. 558–565.

Snider, J., et al., "Characterization of the heterogeneity of polyethylene glycol–modified superoxide dismutase by chromatographic and electrophoretic techniques," *J. Chromatography*, vol. 599, 1992, pp. 141–155.

Tsutsumi, Y., et al., "Molecular design of hybrid tumour necrosis factor alpha with polyethylene glycol increases its anti–tumour potency," *British Journal of Cancer*, vol. 71, 1995, pp. 963–968.

Woghiren, C., et al., "Protected Thiol–Polyethylene Glycol: A New Activated Polymer for Reversible Protein Modification," *Bioconjugate Chemistry*, vol. 4, No. 5, 1993, pp. 314–318.

Yeates, S.G., et al., "Ethylene glycol oligomers," *Makromolekulare Chemie.*, vol. 185, No. 8, Aug. 1984, pp. 1559–1563.

*Primary Examiner*—Sreeni Padmanabhan
(74) *Attorney, Agent, or Firm*—Christensen O'Connor Johnson Kindness PLLC

(57) ABSTRACT

The present invention provides discrete-length polyethylene glycol and polyethylene glycol containing compounds and methods for their preparation.

20 Claims, 14 Drawing Sheets

Methoxy-oxy-carboxyl Compounds

Dicarboxy-oxy Compounds

Diamino-oxy Compounds

Diol-oxy Compounds

General Reaction:

Specific Example

L

Step 1 ↓

H-(-P-L-P-)-H

Step 2 ↓

H-(-P-L-P-L-P-L-P-)-H

Step 3 ↓

H(-P-L-P-L-P-L-P-L-P-L-P-L-P-L-P-)H

*Fig. 5* ns Ser. No. continuation of application Ser. No.
DISCRETE-LENGTH POLYETHYLENE GLYCOLS

CROSS-REFERENCES TO RELATED APPLICATIONS

This application is a continuation of application Ser. No. 09/062,286, filed Apr. 17, 1998 now U.S. Pat. No. 6,294,697, which is a continuation of international application Serial No. PCT/US96/16760, filed Oct. 18, 1996, which claims the benefit of provisional application Ser. No. 60/005,599, filed Oct. 19, 1995.

FIELD OF THE INVENTION

The present invention is generally directed to polyethylene glycols and, more specifically, to discrete-length polyethylene glycols.

BACKGROUND OF THE INVENTION

Polyethylene glycols are a family of polymers produced from the condensation of ethylene glycol, and have the general formula $H(OCH_2CH_2)_nOH$ where n, the number of ethylene glycol groups, is greater than or equal to 4. Generally, the designation of a polyethylene glycol (PEG) includes a number that corresponds to its average molecular weight. For example, polyethylene glycol 1500 refers to a mixture of polyethylene glycols having an average value of n between 29 and 36 and a molecular weight range of 1300 to 1600 grams/mole.

The properties of polyethylene glycols vary with the polymer's molecular weight. Polyethylene glycols have been used in plasticizers, softeners and humectants, ointments, polishes, paper coating, mold lubricants, bases for cosmetics and pharmaceuticals, solvents, binders, metal and rubber processing, permissible additives to foods and animal feed, and laboratory reagents, among others.

Polyethylene glycols are generally linear or branched, neutral polyether molecules that are soluble in water and organic solvents. In addition to the uses noted above, polyethylene glycols have proven to be valuable in many biotechnical and biomedical applications. Polyethylene glycols have been advantageously employed in these applications for their ability to impart water solubilization and surface protective properties, and also because these polymers are only weakly immunogenic.

Polyethylene glycols have also been covalently coupled to proteins to alter their properties in ways that extend their potential uses. Due to in vivo instability, the efficacy of a number of therapeutic proteins is severely limited. While many approaches to stabilization of such proteins have been made, the covalent modification of proteins with hydrophilic polymers such as dextran and polyethylene glycols has been most successful. Typically, polyethylene glycol-protein conjugates are more stable than the native protein in vivo and often, the modified proteins exhibit enhanced resistance to proteolytic degradation. The result is an increase in the therapeutic protein's life in circulation and a reduction in its immunogenicity. In some instances, the therapeutic efficiency of these conjugates is greatly enhanced compared to the native protein.

The improved performance of PEG-modified conjugates has resulted in their development as therapeutic agents. For example, enzyme deficiencies where the native enzyme was ineffective due to its rapid clearance and/or immunological reactions have now been treated with equivalent PEG-enzymes. In fact, PEG-adenosine deaminase has obtained FDA approval. Because PEG-enzymes can act as catalysts in organic solvents, the use of such PEG-enzymes to produce desired stereoisomers offers an advantage to classical organic synthesis which typically produces racemic mixtures of organic products. See, e.g., Degado et al., *Crit. Rev. Ther. Drug Carrier Systems*, Vol. 9, pp. 249–304, 1992.

Examples of polyethylene glycol-modified proteins include PEG-adenosine deaminase (PEG-ADA), which has been used in enzyme replacement therapy for immunodeficiency due to ADA deficiency (M. S. Hershfield, *Clin. Immunol. Immuno. Pathol.*, Vol. 76, S 228–232, 1995); PEG-recombinant human granulocyte colony stimulating factor (PEG-rhG-CSF), which showed an increase in stability and retention of in viva bioactivity and has been suggested as a suitable form of the protein for inclusion in an oral delivery formulation (P.-K. E. Jensen et al., *Pharm. Res.*, Vol. 13, pp. 102–107, 1996); PEG-natural human tumor necrosis factor alpha, which showed a gradual decrease in specific activity with increasing degree of PEG-modification and a drastic increase in plasma half-life upon PEG-modification (Y. Tsutsumi et al., *Br. J. Cancer*, Volume 71, pp. 963–968, 1995); PEG-recombinant human interleukin-2, which retains the in vitro and in vivo activity of interleukin-2, but exhibits a markedly prolonged circulating half-life (T. Menzel et al., *Cancer Bio. Ther.*, Vol. 8, pp. 199–212, 1993); and PEG-asparaginase, which has shown promise in patients suffering from acute lymphocytic leukemia (N. Burnham, *Am. J. Hosp. Pharm.*, Vol. 52, pp. 210–218, 1994). Polyethylene glycol conjugates of oligonucleotides have also been prepared and show a more than tenfold increase in exonuclease stability (A. Jaschke et al., *Nucleic Acids Research*, Vol. 22, pp. 4810–4817, 1994).

Other PEG-modified proteins include papain (C. Woghiren et al., *Bioconjugate Chemistry*, Vol. 4, pp. 314–318, 1993), asialofetuin (L. Roseng et al., *J. Biol. Chem.*, Vol. 267, pp.22987–22993, 1992), collagen (C. J. Doillon et al., *Biomaterial Sciences Polymers*, Vol. 6, pp. 715–728, 1994), RGDT peptides (I. Saiki, *Japanese J. Cancer Research*, Vol. 84, pp. 558–565, 1993), serum IgG (R. Cunningham et al., *J. Immunol. Methods*, Vol. 152, pp.177–190, 1992), alpha 1-proteinase inhibitor (A. Mast et al., *J. Lab. Clin. Med.*, Vol. 116, pp. 58–65, 1990), growth hormone releasing factor (A. Felix, *Int. J. Peptide Protein Research*, Vol. 46, pp. 253–264, 1995), basic fibroblast growth factor (S. Kusstatscher et al., *J. Pharmacol. Exp. Ther.*, Vol. 275, pp. 456–61, 1995), and catalase, uricase, honey bee venom, hemoglobin, and ragweed pollen extract. As indicated by the number of utilities noted above, polyethylene glycol has recently been widely used to develop new therapeutic agents.

Despite the widespread use of polyethylene glycols to modify therapeutic agents, their use has not been without associated disadvantages. The covalent attachment of polyethylene glycol to superoxide dismutase produces a heterogeneous mixture of modified protein species. The heterogeneity of the product derives from, in part, the polydispersity of the polyethylene glycol reagent (J. Snyder et al., *J. Chromatography*, Vol. 599, pp. 141–155, 1992.)

Commercially available polyethylene glycols having molecular weights greater than about 300 grams/mole are available only as mixtures of varying length polymers. The range of PEG polymer lengths results from the polymerization process by which the PEG polymers are prepared. Commercially available PEG polymers include polymers having average molecular weights of 100, 200, 300, 400, 600, 900, 1000, 1500, 2000, 3400, 4600, 8000, and 10000 grams/mole from Aldrich Chemical Co. (Milwaukee, Wis.);

3350 and 20000 grams/mole from Sigma Chemical Co. (St. Louis, Mo.); and 1000, 2000, 3000, 5000, 10000, 20000 and 25000 grams/mole from Shearwater Polymers, Inc. (Huntsville, Ala.). The exact composition of these mixtures are not generally provided, but are considered of relatively narrow range except where terminal monomethyl ethers are desired.

Inherent problems with the utilization of such polymeric mixtures of PEG molecules exist. One of the most significant problems is that a mixture of compounds is obtained when these compounds are modified or used to modify other compounds. Having a mixture of compounds complicates purification and characterization of the compounds. Further, even though PEG molecules are relatively innocuous in the biological system, different compounds within these mixtures are likely to have different pharmacokinetics, pharmacodynamics, and even varying degrees of toxicity, making such a mixture questionable for pharmaceutical applications.

Yet another consideration in having mixtures is the role of sizes in obtaining the desired biological properties. While small differences might be expected in solubilization within a "narrow" average molecular weight range, properties such as rendering proteins nonimmunogenic may be compromised by having a mixture of sizes on the protein surface. The fact that there are variances in lengths may make the protein more recognizable. While immunogenic proteins modified by PEG compounds often have benefits arising from that process, the fact that a mixture of PEG compounds is used may result in obtaining weakly immunogenic responses.

Accordingly, there remains a need in the art for alternatives to PEG polymers composed of a mixture of lengths and molecular weights to overcome the difficulties associated with the preparation, purification, characterization, and therapeutic administration of such PEG mixtures. The present invention seeks to fulfill these needs and provides further related advantages.

SUMMARY OF THE INVENTION

In one aspect of the invention, polyethylene glycol containing compounds of discrete-length are disclosed. In one embodiment, functionalized polyethylene glycol containing compounds are disclosed. In another aspect, the present invention discloses a convergent synthetic method for the preparation of polyethylene containing compounds having discrete-lengths.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 5 is a schematic representation of a synthetic method of the present invention;

DETAILED DESCRIPTION OF THE PREFERRED EMBODIMENT

Figure 1A:
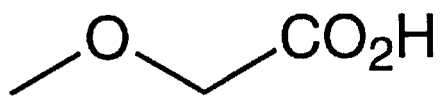
FIG. 1 is an illustration of some commercially available PEG compounds.
Figure 1A:
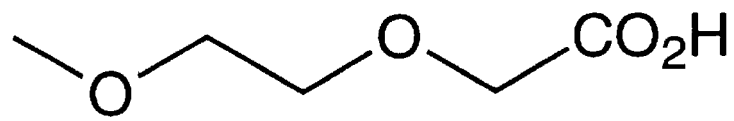
Figure 1A:
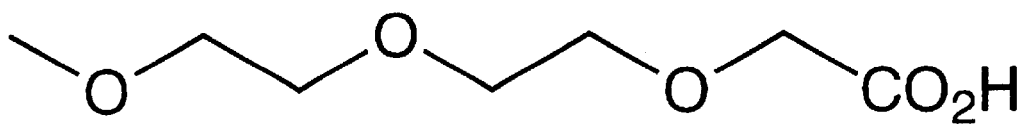
Figure 1B:
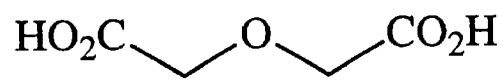
Figure 1B:
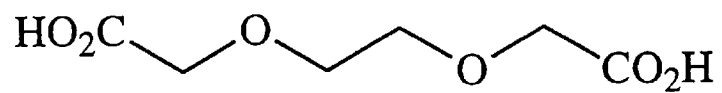
Figure 1B:
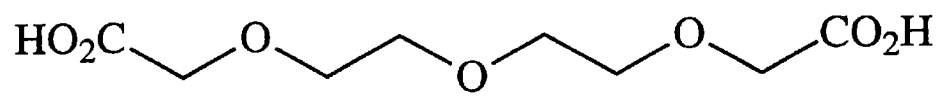
Figure 1C:
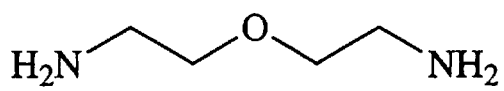
Figure 1C:
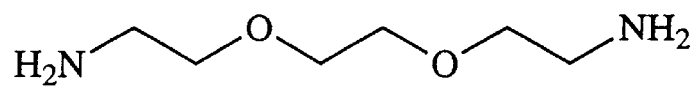
Figure 1C:
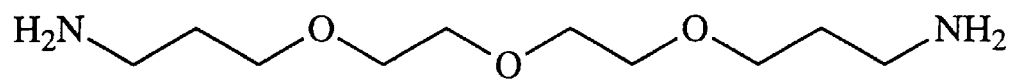
Figure 1D:
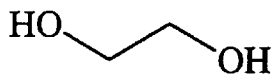
Figure 1D:
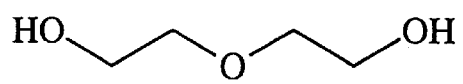
Figure 1D:
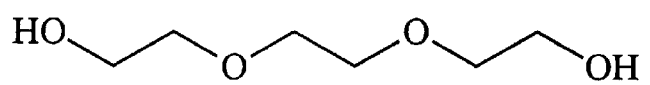
Figure 1D:
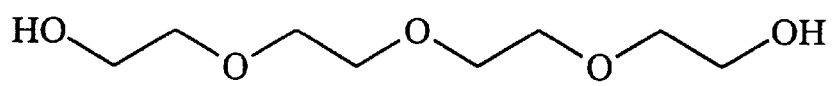
Figure 1D:
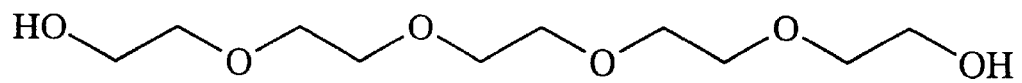

The present invention is generally directed to polyethylene glycol (PEG) and polyethylene glycol containing compounds and compositions and methods related to their preparation and use. More specifically, the present invention is directed to polyethylene glycols and polyethylene glycol containing compounds having a discrete-length and molecular weight. As used herein, the phrase "discrete-length" refers to a polyethylene glycol prepared by a nonpolymeric process such that the polyethylene glycol and have a specific discernible molecular weight. Polyethylene glycols having discernible molecular weights can be contrasted to polymeric processes currently utilized which produce polyethylene glycols having a range of lengths and a range of molecular weights. The present invention provides discrete-length polyethylene glycols, discrete-length polyethylene glycol containing compounds, including polyethylene glycol containing compositions that include the foregoing and methods for the preparation of the same.

One aspect of the present invention provides a polyethylene glycol compound that includes at least one discrete length polyethylene glycol moiety having a molecular weight of at least about 300 grams/mole. Particularly suitable moieties for most uses, generally have a molecular weight in the range of about 1000 to about 50,000 grams/mole, preferably in the range of about 2000 to about 20,000 grams/mole, more preferably in the range of about 2500 to about 7500, specifically about 2500, 3000, 3500, 4000, 4500, 5000, 5500, 6000, and 6500. The discrete length polyethylene glycol moiety generally includes any moiety having a discrete length and molecular weight and includes the repeated ethylene glycol unit (i.e., $-(OCH_2CH_2)_n-$). The repeating unit may be linked by any number of suitable molecules or cross-linking agents described below in detail and may include one or more of the following radicals.

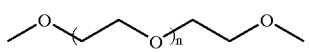

wherein generally, n=1–1000, preferably 45–700, more preferably 50–150, and in a particular preferred embodiment, n=100–125, and

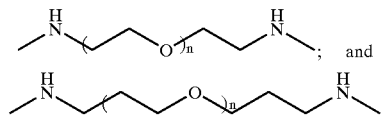

wherein n=1–3.

The radicals noted above are polyethylene glycol and polyethylene glycol containing moieties found in representative polyethylene glycol building blocks, such as those shown in FIG. 1, utilized to produce the compounds of the present invention and further described below.

Suitable polyethylene glycol containing compounds that serve as building blocks (i.e., starting materials and intermediates) for the preparation of the polyethylene glycols and polyethylene glycol containing compounds of the present invention include alkyloxy oxycarboxy compounds having the general formula R O—$(CH_2CH_2O)_n$—$CH_2CO_2H$, where n=0–2; oxy dicarboxy compounds having the general formula $HO_2C$—$CH_2O$—$(CH_2CH_2O)_n$—$CH_2CO_2H$ where n=0–2; oxy diamino compounds having the formula $NH_2$—$(CH_2CH_2O)_n$—$CH_2CH_2NH_2$ where n=1–3 and $NH_2CH_2$—$(CH_2CH_2O)_n$—$CH_2CH_2CH_2NH_2$ where n=1–3; and oxy diol compounds having the formula HO—$(CH_2CH_2O)_n$—$CH_2CH_2OH$ where n=1–4. In one preferred embodiment, the discrete-length polyethylene glycol moiety is a 4,7,10-trioxy-1,13-tridecanediamine radical (the second oxy diamino compound noted above where n=3). In another preferred embodiment, the discrete-length polyethylene glycol moiety is a 3,6,9-trioxyundecanedioic acid radical (the oxy dicarboxy compound noted above where n=2).

In a preferred embodiment, the polyethylene glycol containing compound of this invention includes both a 4,7,10-trioxy-1,13-tridecanediamine radical and a 3,6,9-trioxyundecanedioic acid radical, and has the following formula:

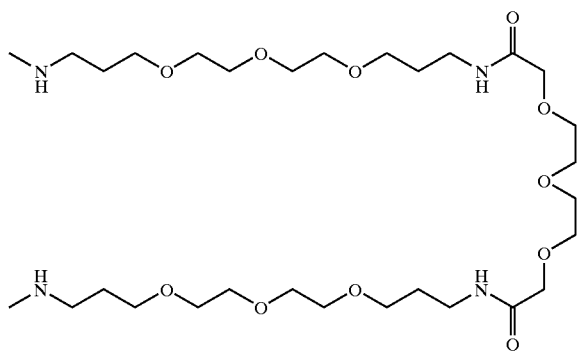

In one embodiment, a polyethylene glycol containing compound of this invention includes a discrete-length polyethylene glycol moiety having at least six polyethylene glycol units and at least one cross-linking agent. Generally, the moiety will have 6–1000 units, preferably 45–700 units, more preferably 50–150 units, and in a particularly preferred embodiment 100–125 units. As used herein, the term "cross-linking agent" includes a chemical compound having at least two reactive or activatable functional groups capable of covalent coupling with suitably reactive discrete-length polyethylene glycol derivatives. The cross-linking agents useful in the present invention preferably do not interfere or significantly reduce the moiety's advantageous PEG characteristics and properties.

The cross-linking agents useful in the present invention include bifunctional, trifunctional, tetrafunctional, or other polyfunctional agents. Preferably, the cross-linking agent is a bifunctional or trifunctional cross-linking agent. Cross-linking agents useful in the present invention include reactive or activatable functional groups that form covalent bonds with the functional groups of the discrete-length polyethylene glycol derivatives. Preferably, the cross-linking agent is a carboxylic acid or a carboxylic acid derivative. Suitable carboxylic acid derivatives include acid halides, acid anhydrides, and activated esters such as, for example, N-hydroxysuccinimide esters, tetrafluorophenyl esters, and p-nitrophenyl esters. In a preferred embodiment, the cross-linking agent is a bifunctional cross-linking agent having the formula:

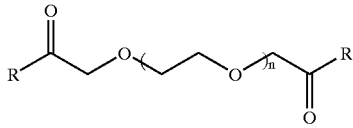

wherein n=0–3, and R is independently selected from —OH, halide, —OCOR' where R' is an aryl or lower alkyl group, activated ester leaving group such as N-hydroxysuccinimide, p-tetrafluorophenol and p-nitrophenol.

In addition to the carboxylic acid cross-linking agents, other cross-linking agents are useful in the methods of the present invention. The cross-linking agent can also include a reactive alkyl moiety, such as an alkyl alcohol that has been derivatized to include a leaving group that may be readily displaced by, for example, an alcohol or amine containing compound. For example, diols substituted with leaving groups may be displaced by polyethylene glycol diols to provide ether linked polyethylene glycols, as shown schematically in FIG. 2. Similarly, suitably substituted diols may be displaced by polyethylene glycol diamines to provide an amine linked polyethylene glycol as shown in the reaction scheme of FIG. 3. The reaction of a dicarboxylic acid cross-linking agent with a polyethylene glycol diol produces an ester linked polyethylene glycol, and reaction with a polyethylene glycol diamine produces an amide linked polyethylene glycol as shown in FIG. 4.

In another aspect, the present invention provides a method for preparing a polyethylene glycol containing compound having a discrete-length polyethylene glycol moiety that has a molecular weight of at least about 300 grams/mole. Generally, the method includes the step of reacting a cross-linking agent with a discrete-length polyethylene glycol derivative having a molecular weight of at least about 300 grams/mole to form a covalent bond between the cross-linking agent and the polyethylene glycol derivative. The general reaction sequence is schematically represented in FIGS. 2–4.

In one embodiment, the method for preparing a polyethylene glycol containing compound of this invention is a convergent synthetic method. By such a method, high molecular weight discrete-length polyethylene glycol containing compounds can be rapidly and efficiently assembled.

Figure 2:
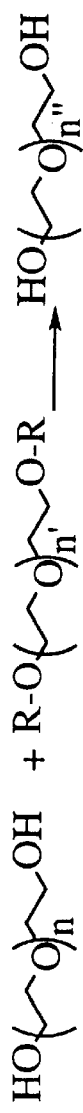
FIG. 2 is a schematic representation of the preparation of a representative discrete-length PEG of the present invention.
Figure 2:
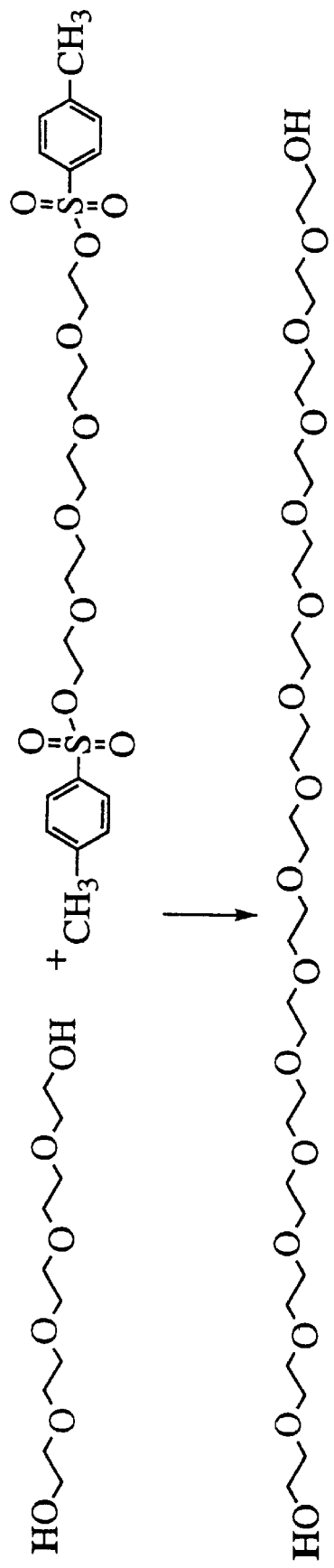
Figure 3:
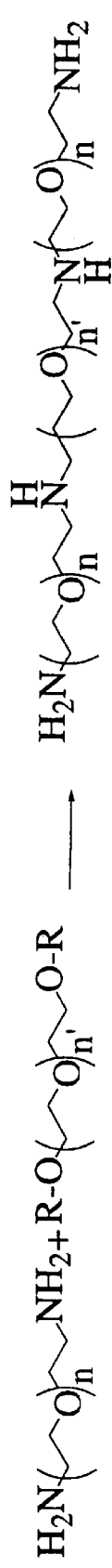
FIG. 3 is a schematic representation of the preparation of a representative amine-linked discrete-length PEG-containing compound of the present invention.
Figure 3:
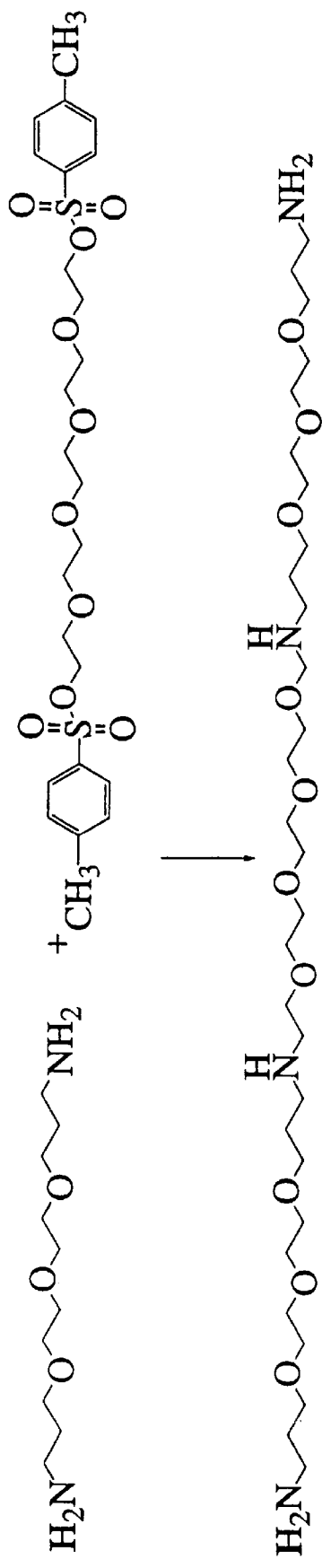
Figure 4:
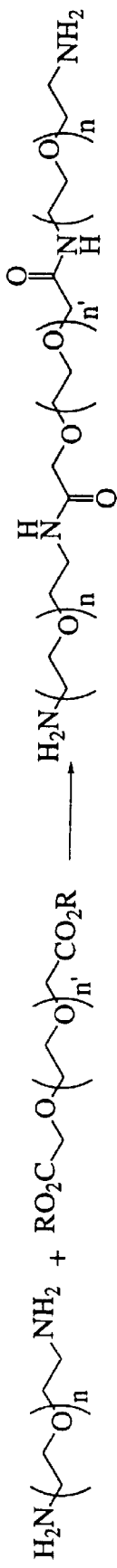
FIG. 4 is a schematic representation of the preparation of a representative amide-linked discrete-length PEG-containing compound of the present invention.
Figure 4:
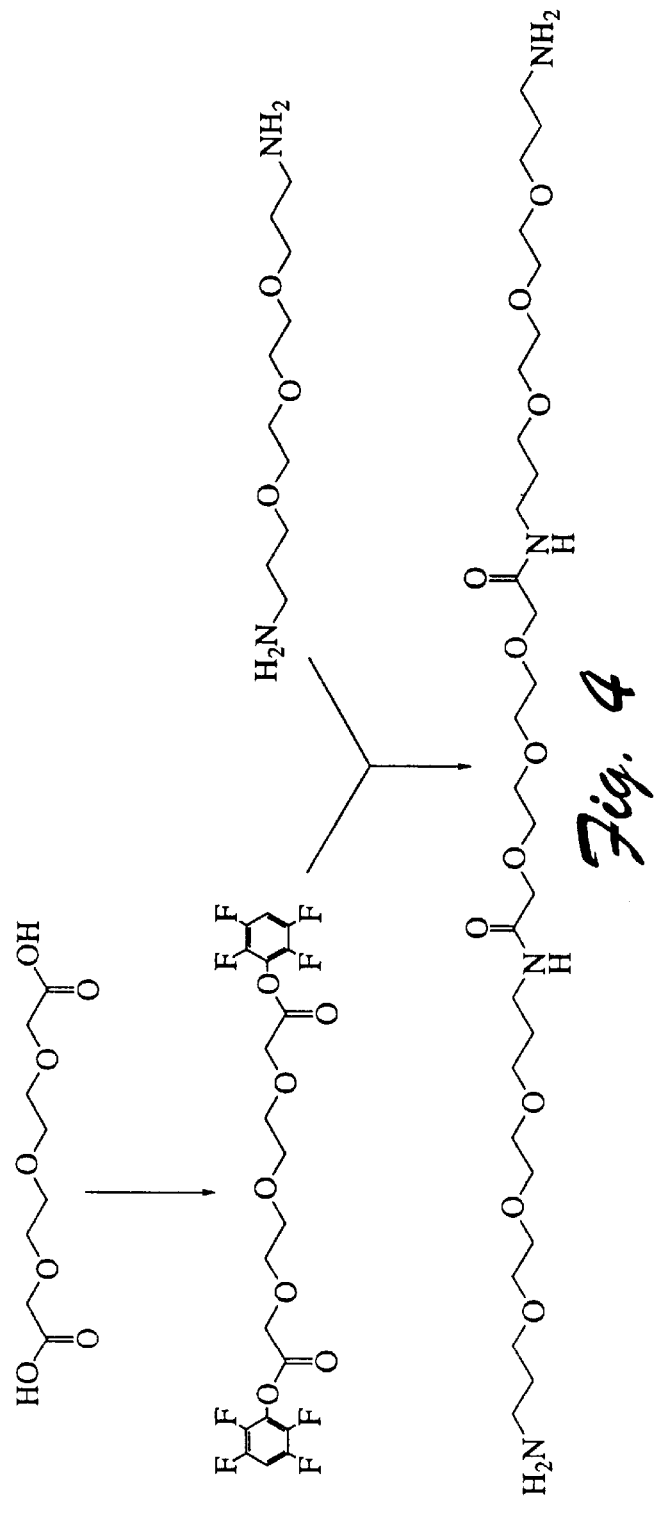

Referring to FIGS. 2–4, discrete-length polyethylene glycol derivatives are added to each functional group of the cross-linking agent in the method. The method of the present invention further includes the additional step of reacting the cross-linking agent with the discrete-length polyethylene glycol (prepared in a previous step) in a repeated manner (i.e., repeated cycles) to rapidly increase the length and molecular weight of the discrete-length polyethylene glycol. Such a method effectively "dimerizes" the starting discrete-length PEG derivative.

A representative example of three-step reaction sequence that provides discrete-length polyethylene glycol containing compounds having molecular weights of about 600, 1400, and 3000, is shown in FIG. 5. Referring to FIG. 5, reaction of a cross-linking agent (i.e., an activated dicarboxylic acid), L, with a diamine, R, produces a discrete-length polyethylene glycol containing compound having a molecular weight of 627 grams/mole. In a second step, the discrete-length polyethylene glycol produced in the first step is reacted with the cross-linking agent. The second step serves to cross-link two discrete-length polyethylene glycol containing compounds produced in the first reaction and provide a discrete-length polyethylene glycol containing compounds having a molecular weight of 1,440 grams/mole. Treatment of the discrete-length polyethylene glycol containing compounds formed by the second step reaction with the same cross-linking agent results in the formation of a discrete-length polyethylene glycol containing compounds having a molecular weight of 3,066 grams/mole. As illustrated by FIG. 5, the method of the present invention provides high molecular weight polyethylene glycols having discrete-lengths in a straightforward synthetic manner (e.g., the formation of a discrete-length polyethylene glycol having a molecular weight of about 3,000 grams/mole from relatively low molecular weight starting materials in three synthetic steps). In a preferred embodiment,

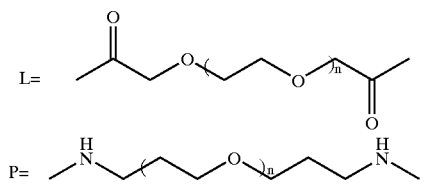

wherein for L, n=0–2, and for P, n=1–3.

As can be seen by the representative reaction sequence shown in FIG. 5, a wide variety of discrete-length polyethylene glycols may be prepared by the method of the present invention by substitution of either one or both of the discrete-length polyethylene glycol building blocks and/or the cross-linking agent. Although FIG. 5 illustrates a preparation of a polyethylene glycol where both the starting materials are polyethylene glycol-containing compounds, it will be appreciated that the present invention includes discrete-length polyethylene glycols prepared from cross-linking agents that include polyethylene glycol functional groups (i.e., —(OCH$_2$CH$_2$)$_n$—) as well as cross-linking agents that do not include polyethylene glycol groups. The use of cross-linking agents other than bifunctional cross-linking agents results in the formation of branched discrete-length polyethylene glycols. Thus, the method of the present invention is versatile and by selection of cross-linking agents provides for the preparation of a wide variety of discrete-length polyethylene glycols. Preferably, the discrete polyethylene glycol containing compounds of the present invention retain the advantageous properties and characteristics of PEG.

The method of the present invention may also be used to prepare a composition that includes a discrete-length polyethylene glycol or PEG containing compound having a molecular weight of at least 300 grams/mole coupled to a second component through a covalent bond. In the method, a polyethylene glycol-containing compound having a discrete-length ethylene glycol moiety of a molecular weight of at least about 300 grams/mole, is reacted with a second component to form a covalent bond. Thus, in one embodiment, the method of the present invention produces a polyethylene glycol derivatized compound by reacting the compound with a discrete-length polyethylene glycol moiety having a molecular weight of at least 300 grams/mole under conditions suitable to form a covalent bond between the polyethylene glycol moiety and the compound.

Figure 7:
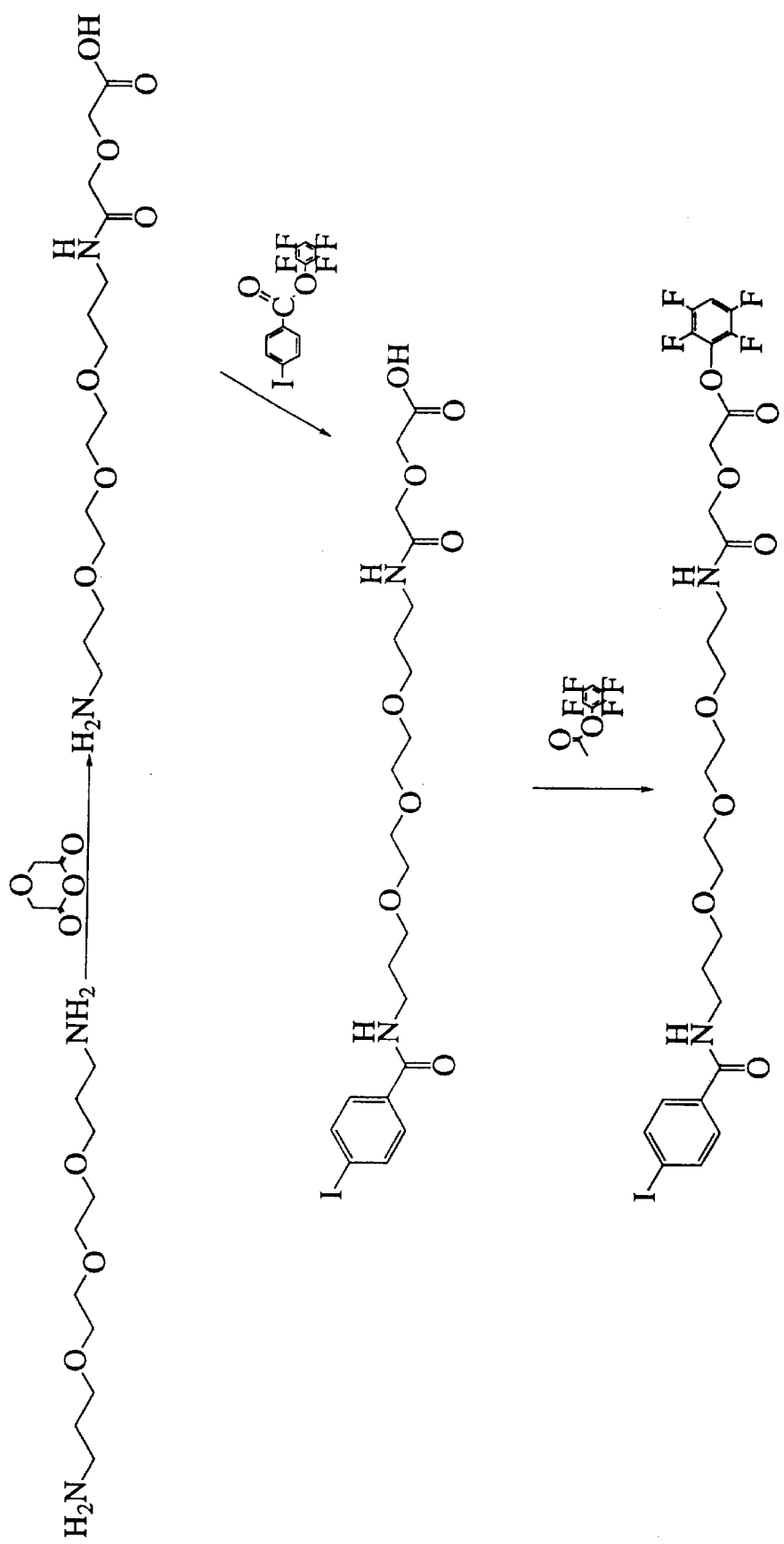
FIG. 7 is a schematic representation of the preparation of a radiolabel PEG building block useful in the preparation of the discrete-length PEG-containing compounds of the present invention.
Figure 8:
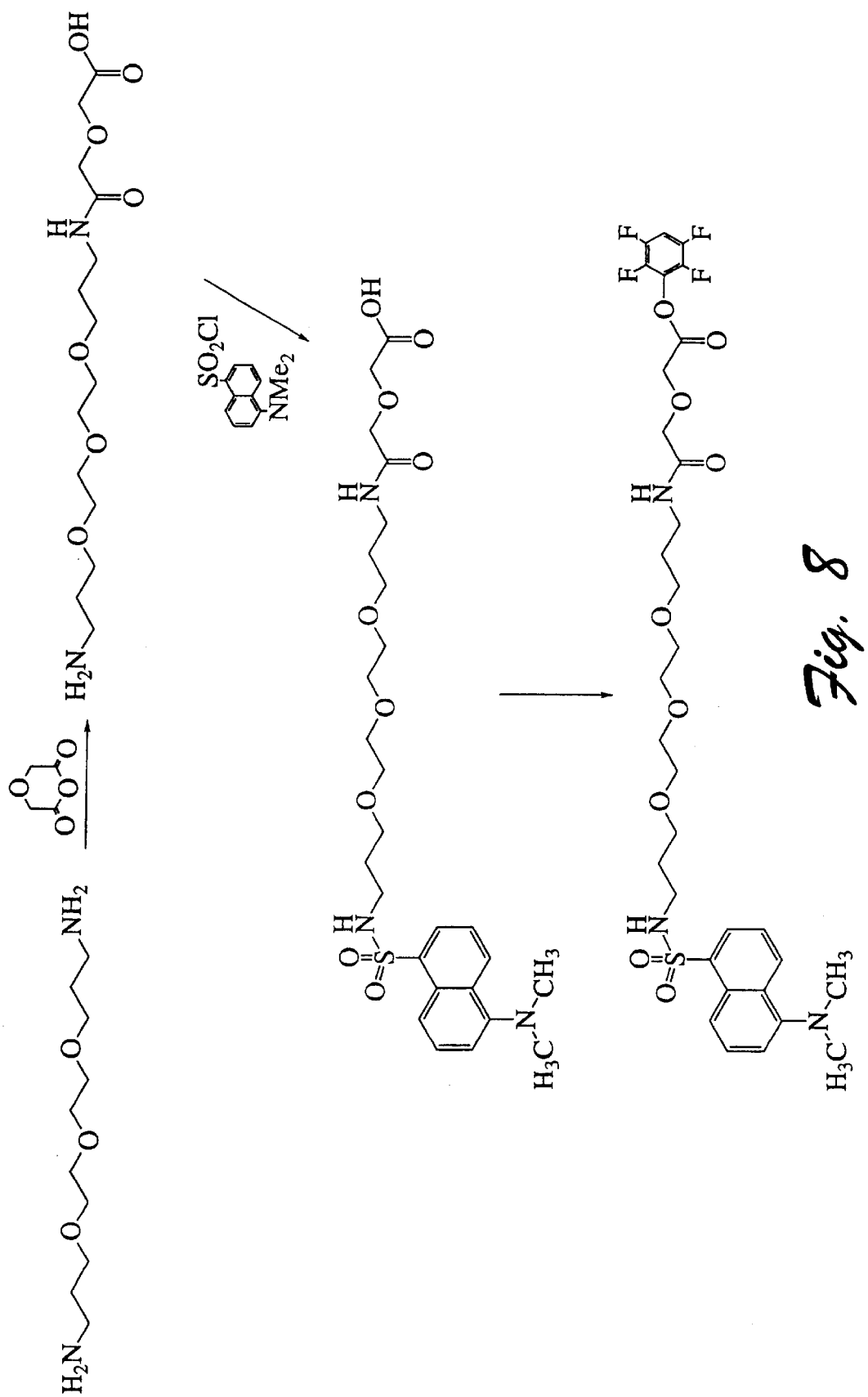
FIG. 8 is a schematic representation of the preparation of a fluorescent label PEG building block useful in the preparation of the discrete-length PEG-containing compounds of the present invention.
Figure 9:
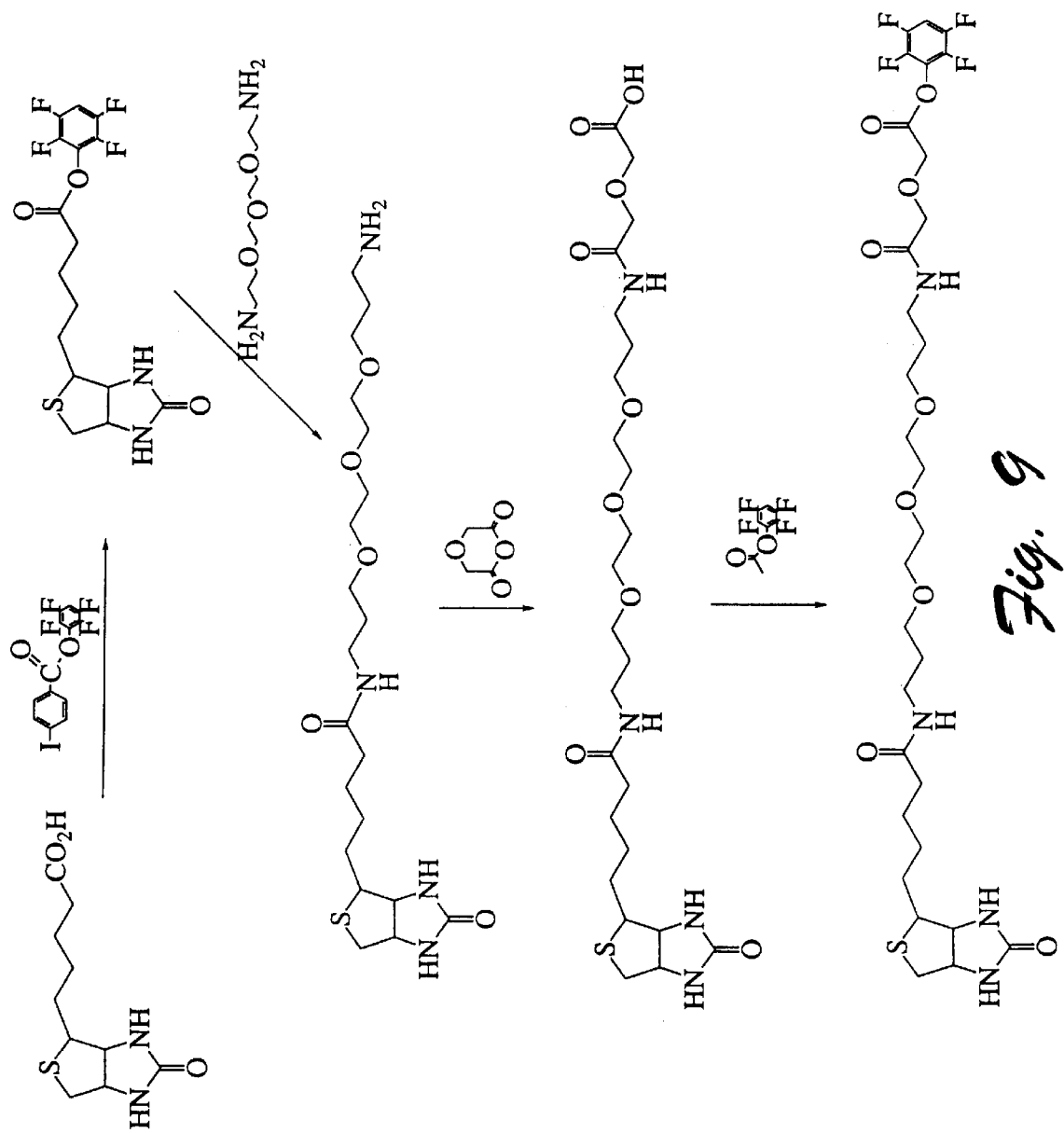
FIG. 9 is a schematic representation of the preparation of a biotin PEG building block useful in the preparation of the discrete-length PEG-containing compounds of the present invention.
Figure 10:
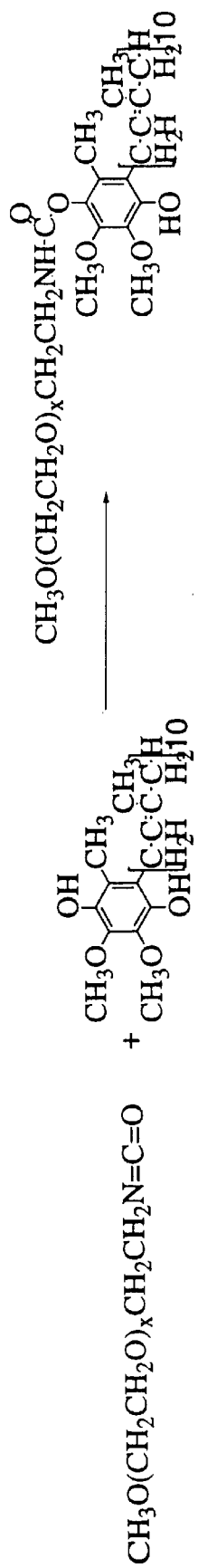
FIG. 10 is the schematic illustration of the preparation of a representative ubiquinone (50) carbamate linked discrete-length PEG containing compound of the present invention.
Figure 11:
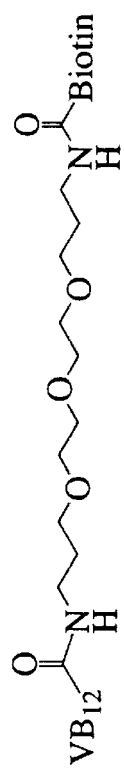
FIG. 11 illustrates representative vitamin $B_{12}$ biotin compositions covalently linked by representative discrete-length PEG-containing moieties of the present invention.
Figure 11:
Figure 11:
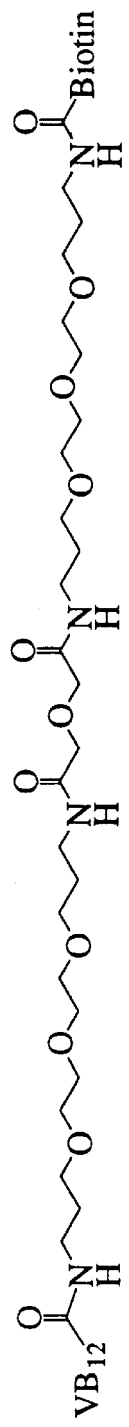
Figure 11:

The compound, or second component, may include any one of a number of compounds including reporter molecules such as radiolabel compounds and precursors to radiolabel compounds, as shown in FIG. 7; a fluorescent compound, as shown in FIG. 8; a protein binding ligand, such as biotin, as shown in FIG. 9; or a therapeutic agent such as ubiquinone 50, as shown in FIG. 10. The discrete-length polyethylene glycols of the present invention may also serve as linkers between two components or compounds. For example, as shown in FIG. 11, discrete-length polyethylene glycols of the present invention can be used to link, for example, vitamin B$_{12}$ to biotin. The discrete-length polyethylene glycol and PEG containing compounds of this invention can also be coupled to hydrophobic moieties to form biphasic compounds useful in the formation of liposomes and micelles.

Because of the well-known water solubilizing properties of polyethylene glycol, the discrete-length polyethylene glycol and PEG containing compounds and composition of the present invention have high water solubility. Accordingly, the polyethylene glycol compounds and compositions of the present invention are particularly useful in solubilizing components that have low solubility in aqueous environments. Furthermore, because of polyethylene glycol's well-known property of stabilizing therapeutic agents in the bloodstream, the discrete-length polyethylene glycol and PEG containing compounds of the present invention may also be useful in stabilizing biologically active molecules including therapeutic agents. The discrete-length polyethylene glycol and PEG containing compounds of this invention may be coupled to therapeutic agents to increase their water solubility, increase their stability in vivo, and to facilitate their administration as water soluble formulations. While the discrete-length polyethylene glycols may be useful in forming compositions with a number of therapeutic agents, preferred therapeutic agents include ubiquinones, particularly ubiquinone 50, and its derivatives, and vitamin B$_{12}$ and its derivatives.

The discrete-length polyethylene glycol containing compounds and compositions of the present invention includes a therapeutic agent covalently attached to the polyethylene glycol through a covalent bond. Where the covalent bond is cleavable and/or degradation of in vivo, the compound or conjugate is a prodrug of the therapeutic agent. Accordingly, the discrete-length polyethylene glycol and PEG containing compounds of the present invention are useful in combination with therapeutic agents as prodrugs and may be effective in the delivery of therapeutic agents such as ubiquinones, vitamin B$_{12}$, and their derivatives.

In another aspect, the present invention provides a pharmaceutical composition that includes a discrete-length polyethylene glycol containing compound or composition having a discrete-length polyethylene glycol moiety with a molecular weight of at least about 300 grams/mole, preferably 2500, 3000, 3500, 4000, or 5000 grams/mole, coupled to a therapeutic agent, and a pharmaceutically acceptable carrier and/or diluent.

The method of the present invention provides a variety of PEG-containing compounds having discrete-lengths, molecular weights, and functional groups. As noted above and described below, the method of the invention provides (a) ether-linked PEG compounds having bis-alcohol termini; (b) amine-linked PEG compounds having bis-amine termini; (c) amide-linked PEG compounds having bis-amine termini; (d) single terminus substituted PEG compounds having, for example, alkyl, radiolabel, fluorescent, and protein binding (e.g., biotin) termini; and (e) PEG compounds substituted at both termini to provide, for example, prodrugs and other linkers, all of which have discrete lengths.

(A) ETHER LINKED—PEG COMPOUNDS—BIS-ALCOHOL TERMINI

In one embodiment, the method of the present invention includes a convergent synthesis that effectively "dimerizes" a discrete-length PEG derivative through a bifunctional cross-linking agent. A general scheme for the preparation of an ether-linked PEG compound having bis-alcohol termini traditional polyethylene glycos (i.e., $H-(OCH_2CH_2)_n-OH$) is represented in FIG. 2. Referring to FIG. 2, the dimerization of a discrete-length PEG diol with a di-activated discrete-length PEG diol is accomplished by using an excess of the first PEG (which can be recycled upon separation from product). The coupling reaction shown employs good leaving groups such as sulfonates (e.g., tosylate, mesylate, triflate). The reaction conditions typically employ a base (e.g., NaH, KOtBu) under conditions generally applied to ether formation. By selecting high molecular starting materials and/or repeating the reaction sequence (i.e., employing additional reaction cycles, as indicated in FIG. 5), the method of this invention can rapidly assemble PEG compounds of discrete-length and molecular weight. For a diol having n ethylene glycol units and a cross-linking agent having n' ethylene glycol units, the product polyethylene glycol has n"=2n+2 ethylene glycol units.

Referring to FIG. 2, an excess of commercially available penta(ethylene glycol) [n=4] may be reacted with commercially available pentaethylene glycol di-p-toluenesulfonate [n'=4] to yield a pentadecane(ethylene glycol) [n"=14]. The same reaction can be conducted, in a second cycle, with the newly generated pentadecane(ethylene glycol) [n"=14] to provide a compound of 34 ethylene glycol units (i.e., $-(CH_2CH_2-O)_{34}-$). When larger derivatives are desired, the PEG diol may be having, for example, pentadecane (ethylene glycol) [n=14] and the PEG ditosylate may be the corresponding di-p-tosylate. The product of such a coupling is a PEG compound having 44 ethylene glycol units. While these compounds are provided by way of example, any size of discrete-length PEG [1<n<500] (commercially available or prepared from a discrete-length compound) may be used to prepare PEG compounds having greater discrete-lengths and molecular weights.

(B) AMINE LINKED PEG COMPOUNDS—BIS-AMINE TERMINI

Substitution of a PEG diamine for the PEG diol in the reaction sequence described above provides an amine-linked PEG, a PEG-like compound that has a-NH-group in place of the —O-group present in traditional polyethylene glycols at the cross-link positions. A general scheme for the preparation of an amine-linked PEG compound having bis-amine termini is represented in FIG. 3. For a diamine having n ethylene glycol units and a cross-linking agent having n' ethylene glycol units, the product amine linked polyethylene glycol has n"=2n+n' ethylene glycol units.

Referring to FIG. 3, an excess of commercially available 4,7,10-trioxa-1,13-tridecanediamine [n=3] is reacted with commercially available pentaethylene glycol p-toluenesulfonate [n'=4] to yield a compound containing 10 ethylene glycol units, two secondary amines and two primary amines. Although the number of ethylene glycol units is decreased over the corresponding simple PEG molecule, the amines will impart water solubility as they will be protonated at neutral pH. The product from this reaction (having a 43-atom length, and molecular weight of 629) can be further reacted to provide a dimer having a molecular weight of about 1500 grams/mole. Further PEG units may be added to these compounds by traditional chemical means to produce even larger PEG compounds.

(C) AMIDE LINKED PEG MOLECULES—BIS-AMINE TERMINI

Substitution of the diactivated diol cross-linking agent in the reaction sequence described above with a diactivated dicarboxylic acid derivative provides an amide linked PEG, a PEG-like compound that has an $-NHCOCH_2-$ group in place of the —O-group present in traditional polyethylene glycols at the cross-link positions. A generalized scheme for the preparation of an amide-linked PEG compound having bis-amine termini is represented in FIG. 4. For a diamine having n ethylene glycol units and a cross-linking agent having n' ethylene glycol units, the product amide-linked polyethylene glycol has n"=2n+n' ethylene glycol units.

Referring to FIG. 4, an excess of commercially available 4,7,10-trioxa-1,13-tridecanediamine [n=3] may be reacted with readily prepared di-tetrafluorophenyl ester of 3,6,9-trioxaundecane dioic acid [n'=2] to yield a PEG containing molecule having the equivalent of 9 PEG units. While the number of PEG units is decreased by introduction of amide bonds, the amide link still has an increased water solubility relative to saturated methylene units. The large advantage of using the amide forming reactions is their relative ease of reaction and the high yields obtained. Such linkage may also be useful for those PEG containing compounds in which cleavable linkages are desirous.

(D) SINGLE TERMINUS SUBSTITUTED PEG COMPOUNDS

The PEG containing compounds and methods of this invention may also be used to prepare PEG containing molecules for attachment to molecules or surfaces where they can impart desired effects including water solubilization or detoxification. In some instances, both ends of the PEG compound may be modified. One end of the PEG compound may be simply "capped" to render it non-reactive in the reaction used to attach the molecule to another for imparting PEG properties. Alternatively, one end of the PEG compound may be capped with a reporter functional molecule such as a fluorescent dye or radiolabeling moiety. Other terminus substitution may provide derivative having moieties that: 1) target tumors through variety of receptor modalities; 2) bind with biologically active proteins; 3) cause the molecule to be excluded from cells; 4) cause it to enter cells; 5) cause it to alkylate other moieties or itself; 6) cause it to target infections; and 7) cause it to otherwise be handled in a manner dissimilar to the PEG derivative without the modification. A generalized scheme for coupling of one end of a discrete-length PEG derivative with a second compound is provided below.

Alkyl Terminated PEG Derivatives

Figure 6:
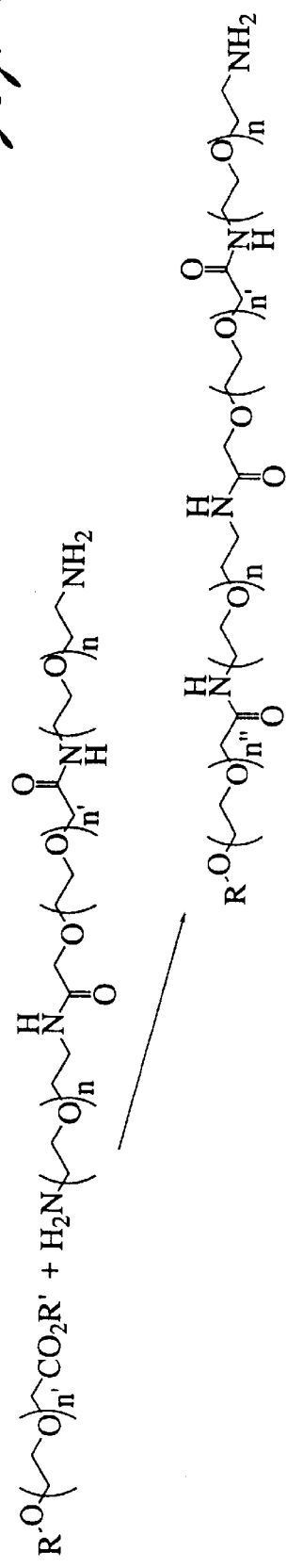
FIG. 6 is a schematic representation of the preparation of a representative alkoxy-terminated discrete-length PEG-containing compound of the present invention.
Figure 6:
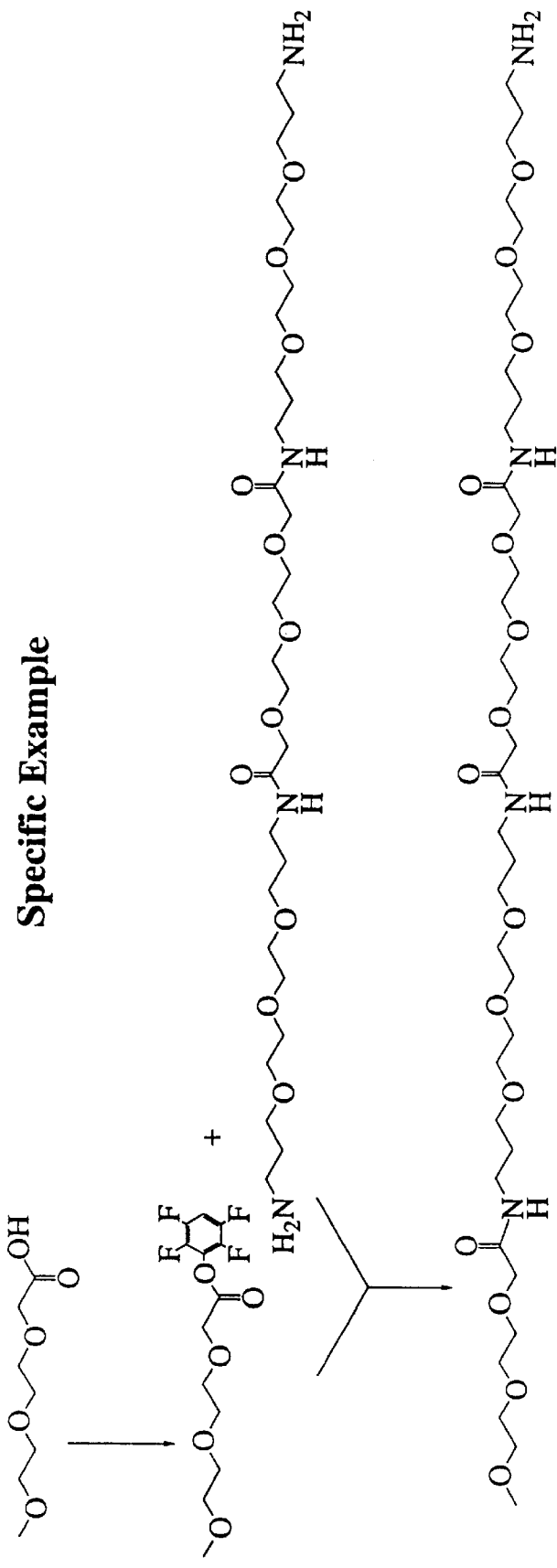

Referring to FIG. 6, the tetrafluorophenyl (TFP) ester of commercially available 2-[2-(2-methoxyethoxy)ethoxy] acetic acid is reacted with an excess of the diaminodiamide nonaoxa product of the specific reaction shown in FIG. 4 to provide a monomethyl terminated PEG containing compound (51 atoms long, MW=787).

Radiolabeled Group (Aryl Iodide) PEG Derivatives

A method for introducing an iodinated phenyl group into a PEG compound is shown in FIG. 7. The TFP ester of p-iodobenzoate is used as the reagent in the second step of the scheme. Replacement of the reagent with the TFP ester of p-tri-n-butylstannylbenzoate provides a compound which can be used to introduce a radioiodine (by substitution of the stannyl group with radioiodine) into a PEG compound. The radioiodination can take place as the last step of any derivatization with the arylstannyl-PEG. The TFP ester may then be reacted with a diamino-PEG containing compounds in a manner as described above for the TFP ester of the methyl terminated PEG in FIG. 6.

Fluorescent Group (Dansyl) PEG Derivatives

A method for introducing a fluorescent group (i.e., dansyl) is shown in FIG. 8. Dansyl chloride is reacted with the diglycolic anhydride adduct of commercially available 4,7,10-trioxa-1,13-tridecanediamine. Activation of the carboxylic acid functionality with tetrafluorophenyl ester is accomplished with the TFP-acetate. The TFP ester is reacted with a diamino-PEG containing compound as described above and illustrated in FIG. 6.

Protein Binding Group (Biotin) PEG Derivatives

A method for introducing a biotin molecule into a PEG derivative is shown in FIG. 9. In the reaction sequence, the biotin carboxylate is activated by preparing the TFP ester, then reacted with commercially available 4,7,10-trioxa-1,13-tridecanediamine. The resultant amino compound is reacted with diglycolic anhydride, and the resultant carboxylate is activated by formation of the TFP ester. The TFP ester is then reacted with a representative diamino-PEG derivative to yield a PEG containing compound having a biotin at one terminus and an amino group at the other terminus.

(E) SUBSTITUTION AT BOTH TERMINUS OF THE DISCRETE-LENGTH PEG CONTAINING MOLECULES

Many examples of PEG containing compounds of interest have both terminus substituted with compounds. Some examples are noted below, but it will be appreciated that the PEG compounds of the present invention may be useful in other applications as well.

Water Solubilizing Prodrugs

The PEG containing compounds of this invention may be prodrugs. The PEG containing compounds of this invention can be used simply to provide enhanced water solubility to compounds and components to which they are coupled. The compounds may further be designed to release the parent compound once it been administered. In some cases, all that is of interest is to have one non-reactive terminus (e.g., methoxy terminated) and a cleavable linkage (e.g., ether, ester, carbamate, carbonate) at the other terminus. An example of this can be made where a highly water insoluble compound, coenzyme $Q_{10}$ (ubiquinone 50), can be made water soluble with PEG derivatives. These derivatives are made wherein the PEG containing compounds are attached to the hydroquinone alcohols produced by gentle reduction of native coenzyme $Q_{10}$. The coupling at a PEG to ubiquinone 50 is shown in FIG. 10, where an isocyanate (produced from a terminal amino group) containing PEG is attached to the hydroquinone through formation of a cleavable carbamate group. The discrete-length PEG containing compounds of this invention are preferred because of the difficulty in purifying and characterizing the product obtained using a mixture of different sized PEG compounds. Other examples where the terminus away from the coenzyme $Q_{10}$ molecule contains a hepatic localizing moiety, a cell membrane permanent agent, a charged species, or a number of other biologically relevant molecules may be prepared as part of the water solubilizing discrete-length PEG containing molecules.

Water Solubilizing Linkers Within Compounds

The PEG containing compounds of this invention may be used as water solubilizing linkers between two compounds that have different biological properties. One such example is the use of the commercially available 4,7,10-trioxa-1,13-tridecanediamine as a water solubilizing linker molecule to conjugate vitamin $B_{12}$ ($VB_{12}$) to biotin. A similar sized (non-PEG containing) linker, 1,12-diaminododecane had been used previously, and the resulting conjugate was found to have low water solubility. However, the conjugate prepared using the PEG containing diamine was found to be quite water soluble. Importantly, PEG containing linkers of greater and discrete length than those available commercially are of interest. Lengthy linkers are advantages to separate the two proteins that bind with vitamin $B_{12}$ and biotin. Examples of several different linkers with discrete-lengths being used as water solubilizing spacer (linker) molecules are shown in FIG. 11. The water solubilization has been found to be particularly important in the preparation and application of vitamin $B_{12}$ dimers. The PEG containing linkers have been shown to improve the water solubility dramatically. FIG. 12 schematically depicts a representative use of the PEG containing compounds as linkers to solubilize compounds having low solubility in aqueous environments.

PEG compounds of this invention have discrete-lengths and molecular weights. These compounds overcome the difficulties of preparing, characterizing and administering mixtures of compounds. Although polymerization is a cost attractive method of making large molecules including PEG compounds, the problems associated with polymer purification ultimately raise the overall costs significantly. Alternatives to polymerization for making long chain compounds include a systematic building of the molecule by a stepwise process (e.g., peptide synthesis) and convergent synthesis, wherein increasingly larger pieces are prepared and combined in a few step process. Generally, a convergent method is preferred for producing PEG containing compounds having discrete-lengths. The convergent synthesis method also provides the advantage of being readily scaled up for production.

Although the PEG containing compounds having discrete-lengths may have physical and biological properties similar to those obtained from PEG mixtures (i.e., nondiscrete-lengths and molecular weights) produced by polymerization processes, the advantages of introducing other functional groups within the discrete-length PEG containing compounds. For example, one advantage of synthesizing discrete PEG containing compounds is that, unlike PEG compounds produced by polymerization, functional groups (e.g., amines) which readily allow derivatization within the polymer chain is possible. Also, it is possible to introduce functional groups within the chain which permit physical or biological degradation of the chain (e.g., peptidase sensitive (amides), esterase sensitive (esters), pH sensitive (carbonates and carbamates), photosensitive groups (aryl nitro compounds), and thermal sensitive groups). The introduction of the cleavable groups within a PEG compound may be used to impart new and valuable control to a variety of processes that these compounds are involved in, including altering the in vivo pharmacokinetics of compounds derivatized with them. A convergent synthesis also has an advantage over polymerization methods as derivatization at either one, or both, ends of the PEG containing molecule is more readily accomplished.

EXAMPLE 1

Synthesis of a Representative Discrete-length Polyethylene Glycol-Containing Compound The preparation of a representative discrete-length polyethylene glycol containing compound of the present invention is described in this example. Briefly, the representative discrete-length PEG containing compound is synthesized by reacting the ditetrafluorophenyl ester (diTFP) of 3,6,9-trioxaundecanedioic acid (a representative cross-linking agent) with 4,7,10-trioxa-1,13-tridecanediamine.

3,6,9-Trioxaundecanedioic acid diTFP ester 3,6,9-Trioxaundecanedioic acid (45 mmol, 10 g) was dissolved in anhydrous DMF (150 mL). Tetrafluorophenol (115 mmol, 19 g) was added followed by 1-ethyl-3-(3-dimethylamino-propyl)carbodiimide (EDC) (108 mmol, 21 g). The reaction was stirred overnight at room temperature, and the solvent was removed under vacuum. The residue was extracted with ether (300 mL) and the ether was washed with saturated sodium bicarbonate solution (3×25 mL), then with water (2×25 mL). The ether solution was dried over anhydrous sodium sulfate and then the ether was removed under vacuum. The resultant product was dried under vacuum at 50–55° C. to yield 15.8 g (76%) of product as an oil.

$^1$H NMR (CDCl$_3$, δ): 3.6–3.8 (m, 8H), 4.46 (s, 4H), 6.9 (m, 2H).

9-Oxadiamine 4,7,10-Trioxa-1,13-tridecanediamine (66 g, 300 mmol) (prepared as described above) was added in a dry flask and a solution of 3,6,9-trioxaundecanedioic acid diTFP ester (15.8 g, 30.5 mmol) in 250 mL of acetonitrile was dripped into it dropwise, at 0° C. over a period of 1 h. The reaction was stirred at room temperature for 1 h and then the solvent was distilled. The residue was stirred with ether and the ether layer was discarded. The crude product was loaded over a silica column and the column was eluted with methanol. The fractions containing product were collected, solvent removed, and the product was dried under vacuum to yield 19 g of g-oxadiamine, a representative discrete-length polyethylene glycol-containing compound of this invention.

$^1$H NMR (MeOH-d$_4$,) δ4.0 (s, 3H), 3.5–3.7 (m, 35H), 3.3 (t, 4H), 2.8 (t, 6H) 1.7–1.8 (m, 10H).

EXAMPLE 2

Synthesis of a Discrete-Length Polyethylene Glycol-containing Compound Coupled to Vitamin B$_{12}$ The preparation of a vitamin B$_{12}$ derivative covalently coupled to a discrete-length polyethylene glycol-containing compound is described. Briefly, the example describes a procedure for the reaction of a cyanocobalamin monocarboxylic acid with the discrete-length polyethylene glycol containing compound prepared as described above in Example 1.

Cyanocobalamin monocarboxylic acid and N-hydroxysuccinimide are dissolved in water and sodium cyanide is added. The discrete-length polyethylene glycol prepared as described in Example 1 is then added and the pH adjusted to 6 with 1 N HCl. N-ethyl-N'-dimethylamino-propyl-carbodiimide-hydrochloride (EDC) is added and the pH of the solution readjusted to 5.5.The reaction mixture is then stirred overnight in the dark at room temperature. In 5 intervals of 6 to 14 h, N-hydroxysuccinimide and EDC are added to the solution, readjusting the pH value to 5.5 each time. After a total reaction time of 4 days (HPLC monitored) the solution is evaporated to dryness, the residue digested with of acetone and the solvent decanted. The solid residue is dissolved in 50 mL of H$_2$O and applied to an Amberlite XAD-2 column. The column is eluted with water, and the desired product is eluted with methanol. The methanol fractions are evaporated to dryness, and the residue dissolved in 25 mL of water and applied to a Dowex Cl$^-$ column. The final product is eluted using water, thereby leaving non-converted acid bound to the column, which is later eluted with 0.04 mol/L sodium acetate buffer pH 4.7. The fractions containing the final product are evaporated to dryness, digested with acetone and filtered. The solid product, a discrete-length polyethylene glycol containing compound coupled to vitamin B$_{12}$, is obtained by recrystallized from aqueous acetone.

EXAMPLE 3

Synthesis of a Discrete-Length Polyethylene Glycol-containing Compound Coupled to Ubiquinone (50)

The preparation of ubiquinone (50) covalently coupled to a discrete-length polyethylene glycol-containing compound is described. Briefly, the example describes a procedure for the reaction of ubiquinone (50) with a suitably reactive form of the discrete-length polyethylene glycol prepared as described above in Example 1.

In a first step, ubiquinone (50) is reduced to the corresponding ubiquinone according Cheng and Casida (*J. Labl. Compd. Radiopharm.*, 6:66–75, 1970). Briefly, a mixture of 1 g of ubiquinone (50), 5 mL of acetic acid and 0.3 g of zinc dust was heated at 50° C. for 5 min., quenched with 5 mL of water and extracted in hexane (45 mL), in an argon atmosphere. Hexane extract was washed with water (3×5 mL), dried over MgSO$_4$, concentrated on a rotoevaporator to obtain 1.10 g of colorless viscous material which was dried at high vacuum (0.05 mm) at room temperature for 1 h to yield 0.980 g of reduced ubiquinone (50). This material is used in the following reactions without further purification.

The ubiquinol prepared as described above can be covalently coupled to various functionalized discrete-length polyethylene glycol-containing compounds to produce a variety of ubiquinone linked PEG-containing compounds having, for example, ether linkages, carbamate linkages, carbonate linkages, and ester linkages.

Ether Linked PEG Compounds

The following procedure provides a general methodology for preparing a ubiquinone having a discrete-length PEG-containing moiety coupled directly to a ubiquinol with an ether linking group.

In a three necked round bottom flask equipped with a dropping funnel and a reflux condenser, ubiquinol (reduced CoQ10 prepared as described above) is dissolved in anhydrous tetrahydrofuran (THF)(added via a syringe) under an argon atmosphere. To this solution is added sodium hydride. The reaction mixture is stirred at room temperature for 15 min., then cooled to 0° C. using an ice bath. To the cooled solution is added a PEG-tresylate, a reactive form of the discrete-length PEG-containing compound prepared as described in Example 1, PEG-tresylate anhydrous tetrahydrofuran via a dropping funnel over a period of 20 min. After stirring the reaction mixture at 0° C., the ice bath is removed and the reaction mixture stirred for an additional 1 h. The reaction mixture is then brought to the reflux temperature by slowly raising the temperature of oil bath to 100° C. After reflux, heating is discontinued and the reaction mixture was allowed to cool to room temperature. The reaction mixture is quenched with a mixture of brine and THF. The solids vacuum filtered and solvent evaporated on a rotoevaporator. The material obtained is dissolved in chloroform and washed with water. The organics dried over anhydrous magnesium sulfate, filtered, concentrated on a rotoevaporator, and dried under vacuum at room temperature to yield a ubiquinone (50) ether linked discrete-length PEG-containing compound.

Carbamate Linked PEG Compounds

The following procedure provides a general methodology for preparing a ubiquinone having a discrete-length PEG-containing moiety coupled directly to a ubiquinol with a carbamate linking group.

The following synthesis of CoQ10-carbamate-PEG is a two-step process. In the first step, the succinimidyl carbamate of the discrete-length PEG-containing compound prepared as described in Example 1 prepared by dissolving dry dioxane and warming to 50° C. to achieve solution. To the cooled solution is added a solution of N,N'-disuccinimidyl carbonate in acetone. A solution of dimethylaminopyridine in acetone is then added and the resulting reaction mixture stirred overnight at room temperature. The crude product is precipitated from the solution by the addition of diethyl ether, filtered, and dried at under vacuum at room temperature to yield the succinimidyl carbamate of the PEG.

In a flask equipped with a dropping funnel and argon balloon was added ubiquinol (reduced CoQ10 prepared as described above) in anhydrous tetrahydrofuran. To this solution is added sodium hydride. The reaction mixture is stirred at room temperature, then cooled to 0° C. using an ice bath. To the cooled solution is added 500 mg the succinimidyl carbamate PEG, prepared as described above, in anhydrous tetrahydrofuran via a dropping funnel. After stirring the reaction mixture at 0° C., the reaction mixture is quenched with a mixture of brine and THF, and the solvent evaporated on a rotoevaporator. The crude product is taken up in 50 mL of chloroform and washed with water (2×10 mL). The organics are dried over anhydrous magnesium sulfate, filtered, concentrated on a rotoevaporator, and dried under vacuum at room temperature to yield the end product.

The crude product is loaded on a flash silica column and eluted with chloroform as the solvent. CoQ10 and other related impurities are eluted with chloroform and the PEG product is eluted with 50% methanol in chloroform to yield a ubiquinone (50) carbamate linked discrete-length PEG-containing compound.

Carbonate Linked PEG Compounds

The following procedure provides a general methodology for preparing a ubiquinone having a discrete-length PEG-containing moiety directly to a ubiquinol with a carbonate linking group. Treatment of a succinimidyl carbonate of the discrete-length PEG-containing compound prepared as described in Example 1 with reduced coenzyme $Q_{10}$ in the presence of appropriate base (such as sodium hydride) in appropriate solvent (such as tetrahydrofuran) provides a ubiquinone (50) carbonate linked discrete-length PEG-containing compound.

Ester Linked PEG Compounds

The following procedure provides a general methodology for preparing a ubiquinone prodrug having a solubilizing moiety coupled directly to a ubiquinol with an ester linking group.

Treatment of reduced coenzyme Q10 with an N-hydroxysuccinimidyl active ester of a succinimide derivative of the discrete-length PEG-containing compound prepared as described in Example 1 in the presence of appropriate base (such as triethylamine or pyridine) in appropriate solvent (such as tetrahydrofuran) provides a ubiquinone (50) ester linked discrete-length PEG-containing compound.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An oxyethylene-containing compound, comprising the reaction product of:

a) at least one discrete oxyethylene-containing crosslinking moiety, wherein said crosslinking moiety comprises three reactive groups; and b) at least two oxyethylene-containing moieties, wherein said oxyethylene-containing moieties are discrete, the oxyethylene-containing moieties being covalently coupled to the crosslinking moiety.

2. The compound of claim 1, wherein the oxyethylene moiety comprises a radical selected from the group consisting of

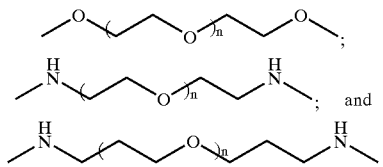

radicals, wherein n=1–3.

3. The compound of claim 1, wherein the oxyethylene moiety comprises a 4,7,10-trioxa-1,13-tridecane diamine radical.

4. The compound of claim 1, wherein the oxyethylene moiety comprises a 3,6,9-trioxaundecanedioic acid radical.

5. The compound of claim 1, wherein the oxyethylene moiety comprises a radical selected from the group consisting of

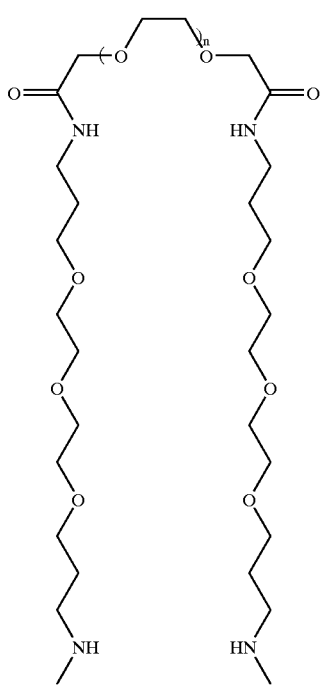

radicals, wherein N=0–2.

6. A pharmaceutical composition, comprising the compound of claim 1 and a pharmaceutically acceptable carrier.

7. A compound, comprising a first component coupled to an oxyethylene-containing linker through a first covalent bond, wherein the oxyethylene-containing linker comprises the reaction product of:
  a) at least one discrete oxyethylene-containing crosslinking moiety wherein said crosslinking moiety comprises three reactive groups, and
  b) at least two oxyethylene-containing moieties, wherein said oxyethylene-containing moieties are discrete, the oxyethylene-containing moieties being covalently coupled to the crosslinking moiety.

8. The compound of claim 7, wherein the first component comprises a therapeutic agent.

9. A method for preparing an oxyethylene-linked compound, comprising:
  reacting a crosslinking agent having three reactive groups with an oxyethylene-containing compound to form an oxyethylene linker having a first covalent bond between the crosslinking agent and the oxyethylene-containing compound, wherein the oxyethylene-containing compound is discrete; and
  reacting the oxyethylene linker with a first component to form a second covalent bond between the oxyethylene linker and the first component.

10. A method for preparing an oxyethylene-containing compound, comprising:
  reacting a first crosslinking agent having three reactive groups with a first oxyethylene-containing compound to form a second oxyethylene-containing compound having a first covalent bond between the first crosslinking agent and the first oxyethylene-containing compound, wherein the first oxyethylene-containing compound is discrete; and
  reacting the second oxyethylene-containing compound with a second crosslinking agent to form a second covalent bond between the second crosslinking agent and second oxyethylene-containing compound to form the oxyethylene-containing compound.

11. An oxyethylene-containing compound, comprising the reaction product of:
  a) at least one discrete oxyethylene-containing crosslinking moiety, wherein said crosslinking moiety comprises four reactive groups; and
  b) at least two oxyethylene-containing moieties, wherein said oxyethylene-containing moieties are discrete, the oxyethylene-containing moieties being covalently coupled to the crosslinking moiety.

12. The compound of claim 11, wherein the oxyethylene moiety comprises a radical selected from the group consisting of

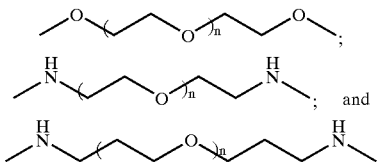

radicals, wherein n=1–3.

13. The compound of claim 11, wherein the oxyethylene moiety comprises a 4,7,10-trioxa-1,13-tridecane diamine radical.

14. The compound of claim 11, wherein the oxyethylene moiety comprises a 3,6,9-trioxaundecanedioic acid radical.

15. The compound of claim 11, wherein the oxyethylene moiety comprises a radical selected from the group consisting of

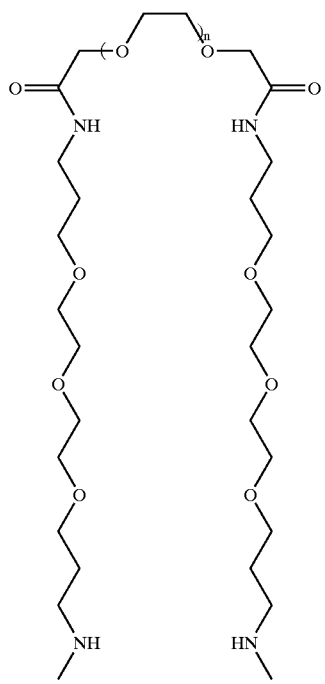

radicals, wherein n=0–2.

16. A pharmaceutical composition, comprising the compound of claim 11 and a pharmaceutically acceptable carrier.

17. A compound, comprising a first component coupled to an oxyethylene-containing linker through a first covalent bond, wherein the oxyethylene-containing linker comprises the reaction product of:

a) at least one discrete oxyethylene-containing crosslinking moiety wherein said crosslinking moiety comprises four reactive groups, and b) at least two oxyethylene-containing moieties, wherein said oxyethylene-containing moieties are discrete, the oxyethylene-containing moieties being covalently coupled to the crosslinking moiety.

18. The compound of claim 17, wherein the first component comprises a therapeutic agent.

19. A method for preparing an oxyethylene-linked compound, comprising:

reacting a crosslinking agent having four reactive groups with an oxyethylene-containing compound to form an oxyethylene linker having a first covalent bond between the crosslinking agent and the oxyethylene-containing compound, wherein the oxyethylene-containing compound is discrete; and reacting the oxyethylene linker with a first component to form a second covalent bond between the oxyethylene linker and the first component.

20. A method for preparing an oxyethylene-containing compound, comprising:

reacting a first crosslinking agent having four reactive groups with a first oxyethylene-containing compound to form a second oxyethylene-containing compound having a first covalent bond between the first crosslinking agent and the first oxyethylene-containing compound, wherein the first oxyethylene-containing compound is discrete; and reacting the second oxyethylene-containing compound with a second crosslinking agent to form a second covalent bond between the second crosslinking agent and second oxyethylene-containing compound to form the oxyethylene-containing compound.

* * * * *